United States Patent [19]
Zhao

[11] Patent Number: 5,970,976
[45] Date of Patent: Oct. 26, 1999

[54] APPARATUS AND METHOD FOR GENERATING PRESSURE CHANGES IN A MAMMALIAN ORAL/THROAT CAVITY

[76] Inventor: Hongwei Zhao, 977 Thompson Blvd., Windsor Ontario N8S 2G7, Canada

[21] Appl. No.: 09/052,569

[22] Filed: Mar. 31, 1998

[51] Int. Cl.$^6$ .................................................. A61M 16/00
[52] U.S. Cl. ............................... 128/204.23; 128/204.21; 600/529
[58] Field of Search ............... 128/204.23, 204.21, 128/204.22, 200.24, 202.16, 205.19, 848; 600/529, 543

[56] References Cited

U.S. PATENT DOCUMENTS

| | | | |
|---|---|---|---|
| 5,632,281 | 5/1997 | Rayburn | 128/719 |
| 5,803,066 | 9/1998 | Rapoport et al. | 128/204.23 |
| 5,873,361 | 2/1999 | Hakala | 128/204.23 |
| 5,875,777 | 3/1999 | Eriksson | 128/204.21 |

*Primary Examiner*—John G. Weiss
*Assistant Examiner*—Charles W. Anderson
*Attorney, Agent, or Firm*—Harness, Dickey & Pierce, P.L.C.

[57] ABSTRACT

Predetermined pressure changes in the oral and throat cavity is achieved by inducing at least a partial vacuum in the mouth and throat area of a mammal in temporal coordination with the mammal's breathing pattern. The partial vacuum is selectively applied to the mouth and throat cavity only during inhalation cycles of the breathing pattern. A further aspect of the invention provides for additionally inducing a positive or atmospheric pressure in the mouth and throat cavity only during exhalation cycles of the breathing pattern.

12 Claims, 3 Drawing Sheets

APPARATUS AND METHOD FOR GENERATING PRESSURE CHANGES IN A MAMMALIAN ORAL/THROAT CAVITY

FIELD OF THE INVENTION

This invention relates generally to methodology and apparatus for establishing predetermined vacuum or pressure levels in the mouth and throat cavity of a mammalian body, such as that of a human, in coordination with the mammal's respiratory pattern.

BACKGROUND OF THE INVENTION

This invention is based on my discovery that respiration-regulated air pressure, either positive or negative (vacuum), in a person's mouth and throat cavity, produces beneficial effects to the person's health such as alleviation of throat discomfort and snoring. The hypothetical explanation of this finding is that respiration-regulated air pressure in a person's mouth and throat cavity stimulate the body's autonomic nervous system, circulatory system, and especially lymphatic system and therefore enhances certain physiological functions, such as lymphatic flow. The body's autonomic nervous system, circulatory system, and lymphatic system are all responsive to pressure changes in the respiration system while a person is inhaling and exhaling. For example, J. W. Shields has conducted a study on the effects of breathing on the lymphatic system. Using cameras inside the body, he found that deep, diaphragmatic breathing stimulated the cleansing of the lymph system by creating a vacuum effect which draws lymph through the bloodstream. See *Human Central Lymph Propulsion*, JAMA, Vol. 246, No. 18, Nov. 6, 1981, Shields, et al.

SUMMARY OF THE INVENTION

Accordingly, in one aspect of the invention, a method for inducing pressure changes in the mouth and throat cavity of a mammal includes the steps of monitoring a respiration pattern of the mammal to determine a first time period during which the mammal is inhaling and a second time period during which the mammal is exhaling. A partial vacuum is induced in the mammal's mouth and throat cavity during the first time period and the partial vacuum is removed during the second time period.

In another aspect of the invention apparatus for inducing pressure changes in the mouth and throat cavity of a mammal includes a regulated vacuum source having an outlet and a control input, an appliance in fluid communication with the outlet of the vacuum source, the appliance adapted for placement in a mouth of a mammal so as to be in fluid communication therewith. A sensor, adapted to be coupled at a preselected portion of the mammal's anatomy and operative to generate a first signal whenever the mammal inhales and a second signal whenever the mammal exhales, signals a controller having an output coupled for controlling the output of the vacuum source. The controller has at least one input coupled for receipt of the first and second signals from the sensor. The controller is operative upon receipt of the first signal to cause the vacuum source to pull at least a partial vacuum in the appliance. The controller is operative upon receipt of the second signal to cause removal of the partial vacuum from the appliance.

BRIEF DESCRIPTION OF THE DRAWINGS

The objects and features of the invention will become apparent from a reading of a detailed description taken in conjunction with the drawings, in which.

DETAILED DESCRIPTION

Figure 1:
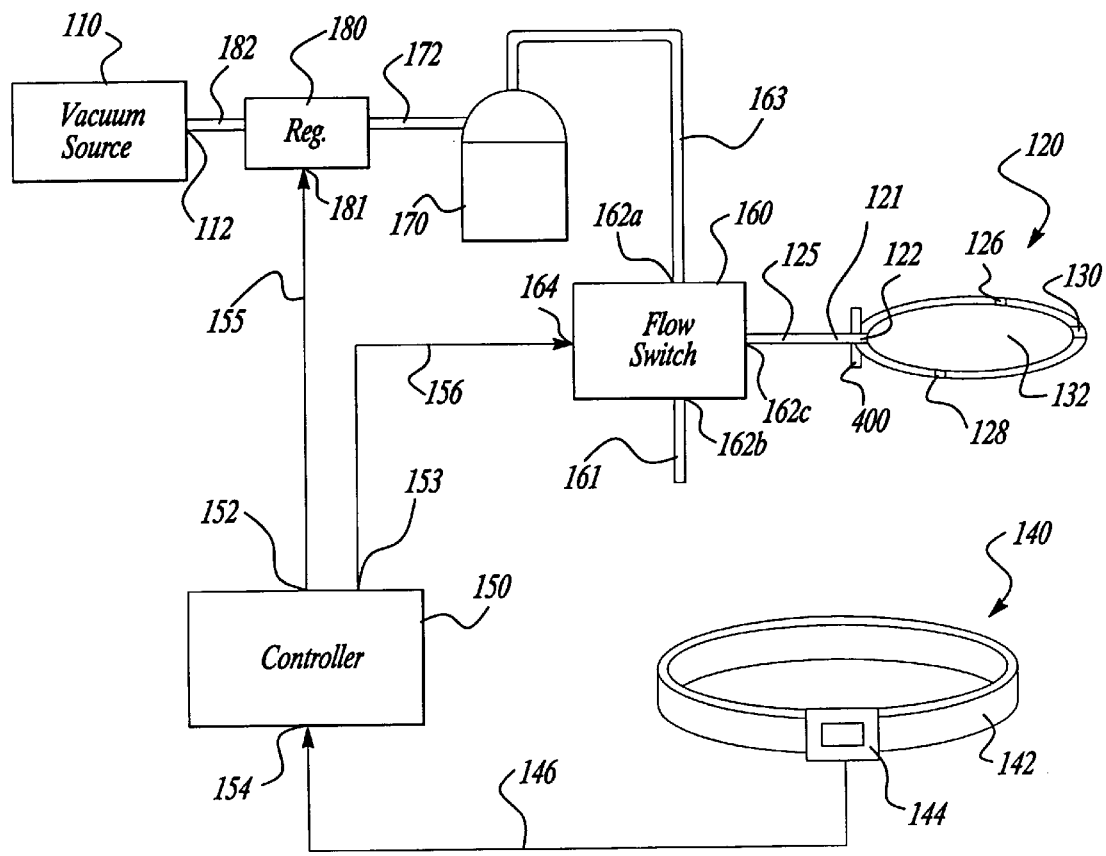
FIG. 1 is a functional block diagram of a first embodiment of a system arranged in accordance with the principles of the invention.

FIG. 1 sets forth a functional diagram of apparatus arranged in accordance with the invention. System 100 includes a vacuum source or pump 110 having an outlet 112 coupled to a first end of a conduit 182. An opposite end of conduit 182 is coupled to an inlet of regulator 180. An output of regulator 180 is coupled via conduit 172 to a vacuum chamber 170. Chamber 170 is coupled via conduit 163 to a first port 162a of fluid flow valve or fluid switch 160. A second port 162b of switch 160 is vented to the atmosphere via conduit 161. Port 162c of switch 160 is coupled via a preferably flexible conduit 125 to an inlet port 122 of oral appliance or appliance element 120 which is sized and shaped for facile insertion into the mouth of an individual.

Appliance 120 is substantially disk shaped and has a hollow interior 132 in fluid communication with the conduit 125 via appliance inlet 122. Additionally a plurality of passages 126, 128 and 130 are arranged in a preselected pattern on at least one side of appliance 120 for providing fluid communication between interior 132 of appliance 120 and the mouth and throat cavity of the individual.

Sensor 140, for generating an indication of whether or not the individual is inhaling or exhaling, includes a belt 142 for engagingly surrounding the abdominal cavity of the user. Ends of the belt 142 terminate at a sensor element 144 which is operative to generate signals indicating inhaling and exhaling. The signals are coupled via bus 146 to an input 154 of a controller 150. Controller 150 may, for example, take the form of a stored program type controller such as a microprocessor-based element. Output 152 of controller 150 is coupled via bus 155 to a control input 181 of regulator 180. A second output 153 of controller 150 is coupled via bus 156 to a control input 164 of fluid switch 160.

In operation, system 100 generates desired pressure levels by having the individual utilizing the system insert the appliance 120 into the oral cavity and by strapping belt 142 about the individual's abdominal cavity. Upon inhaling in the midst of a normal breathing pattern, an appropriate signal is developed by sensor 144 and coupled to controller 150. Controller 150, via bus 155, enables regulator 180 to regulate the output 112 of vacuum source 110 at a preselected vacuum level. Upon receipt of the inhaling indication signal, controller 150 signals switch 160 via bus 156 to fluidly couple port 162a to port 162c thereby enabling at least a partial vacuum to be pulled at the interior 132 of appliance 120 via conduit 125. This partial vacuum is extended into the mouth and throat cavity via passages 126, 128 and 130. Upon cessation of the inhaling cycle and initiation of the exhaling cycle of the breathing pattern, an appropriate signal at sensor 144 is coupled to controller 150 which signals switch 160 via bus 156 to switch port 162c from its fluid connection to port 162a over to port 162b, thereby venting conduit 125 and appliance 120 to the atmosphere via conduit 161. It has been found that a coordinated application of such a vacuum pressure to an individual during the inhalation process produces beneficial results such as alleviation of throat discomfort.

Vessel 170 serves dual functions of 1) acting as an intermediate vacuum chamber and 2) collecting any liquid which is inadvertently entrained in the air fluid flow in the conduit system.

Figure 2:
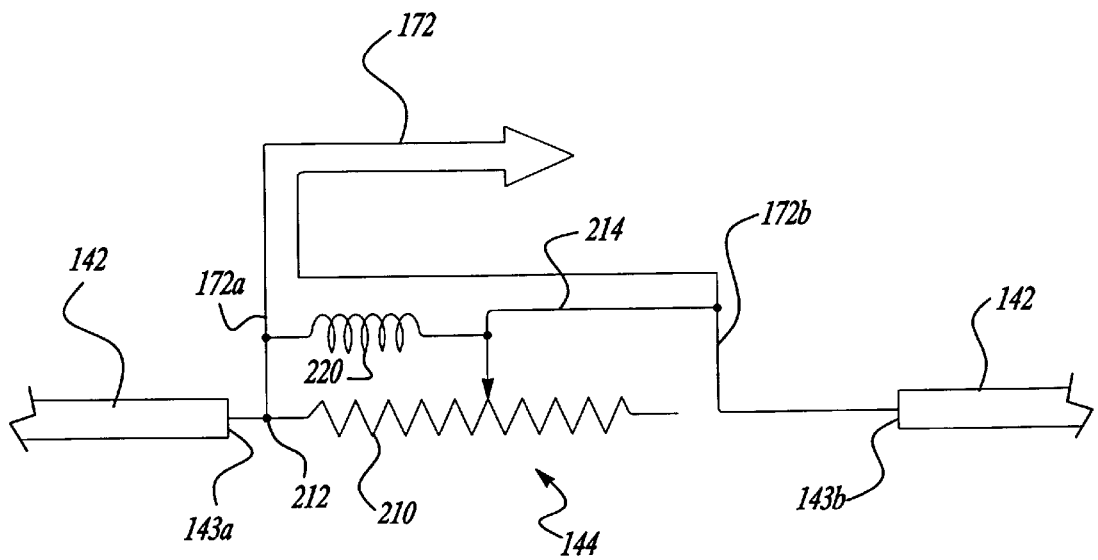
FIG. 2 is a functional schematic of sensor element suitable for use in the system of FIG. 1.

One example of sensor 144 of the system of FIG. 1 is set forth in further detail in the diagram of FIG. 2. Sensor 144 includes a variable impedance element such as a variable resistor 210 having a fixed terminal 212 coupled to a first end 143a of belt 142 and movable terminal 214 coupled to a second end 143b of belt 142.

Additionally attached between the first terminal 212 and second terminal 214 of resistor 210 is a return bias spring 220.

The value of the variable resistance exhibited between terminals 212 and 214 is coupled to input 154 of controller 150 via leads 172a and 172b of bus 172.

As seen from the details of FIG. 2, when the individual wearing belt 142 inhales, the abdominal cavity expands which pulls ends 143a and 143b of belt 142 further apart. This movement, in turn, causes the wiper or movable terminal 214 of resistor 210 to move toward the right as seen in the view of FIG. 2, thus exhibiting a positive change in the resistance presented to terminals 172a and 172b of bus 172. Conversely, when the inhalation period ends and exhalation begins, then the user's abdominal cavity will contract and the return spring element 220 will pull the movable terminal 214 back toward the rest position or to the left as shown in FIG. 2. Hence, during this cycle a negative resistance change is exhibited at terminals 172a and 172b.

These positive and negative electrical resistance value changes are monitored by the controller 150. For example, a microprocessor could be programmed to sample the electrical resistance presented via bus 172 ten times per second. The controller would enter a working condition after five stable cycles of breathing pattern were established. At this point, the controller would enable the vacuum pump 110 via regulator 180 only when controller 150 observes a positive change in resistance at input 154 of controller 150.

Figure 5:
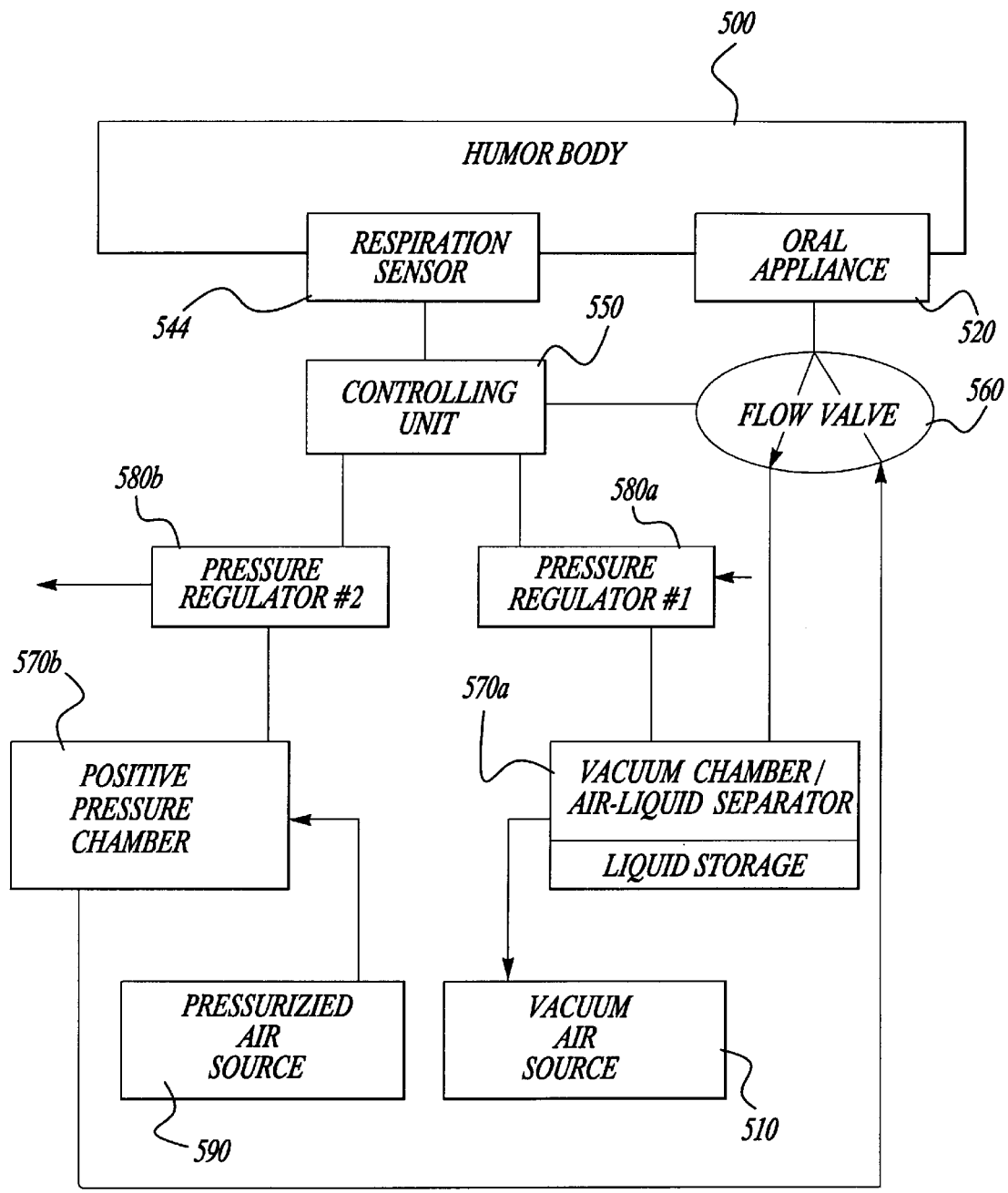
FIG. 5 is a functional block diagram of an alternative embodiment of the invention.

The timing diagram of FIG. 5 sets forth the change in resistive impedance exhibited by sensor 144 along axis 506 versus time along axis 507. Controller 150 enters a working routine after recognizing a predetermined number (e.g. 10) of stable or constant respiration pattern cycles.

During expiration phase 501, the sensor's resistance change is negative which leads to action by controller 150 to inhibit the pulling of a partial vacuum in oral appliance 120. In transition phase 502 where no resistance changes are observed, controller 150 continues inhibiting the pulling of a partial vacuum in appliance 120. However, if controller 150 determines that phase 502 has extended for a time period indicating abnormality of the breathing pattern, such as is found during sleep apnea, controller 150 may initiate re-application of partial vacuum prior to the end of phase 502. During inspiration phase 503, controller 150 enables the pulling of a partial vacuum at appliance 120. This pattern will continue for so long as a stable breathing pattern of predetermined minimum length is maintained. A stable breathing pattern may be defined as one exhibiting not only a steady overall breathing cycle time 505, but also having intermediate periods 502 and 504, which are of predetermined minimum durations wherein neither inhalation nor expiration are occurring.

Figure 3A:
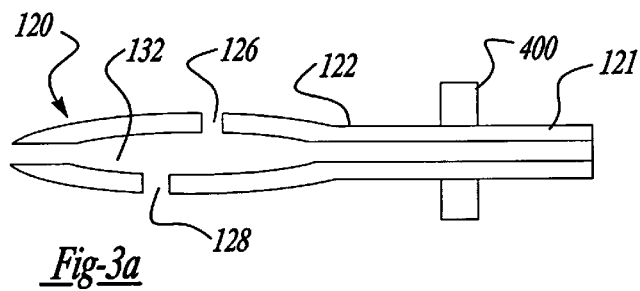
FIGS. 3A and 3B are side and top cross sectional views of an oral appliance arranged in accordance with the principles of the invention.
Figure 3B:
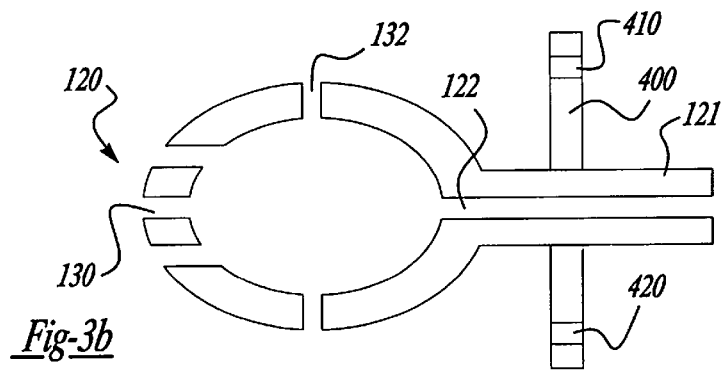
Figure 4:
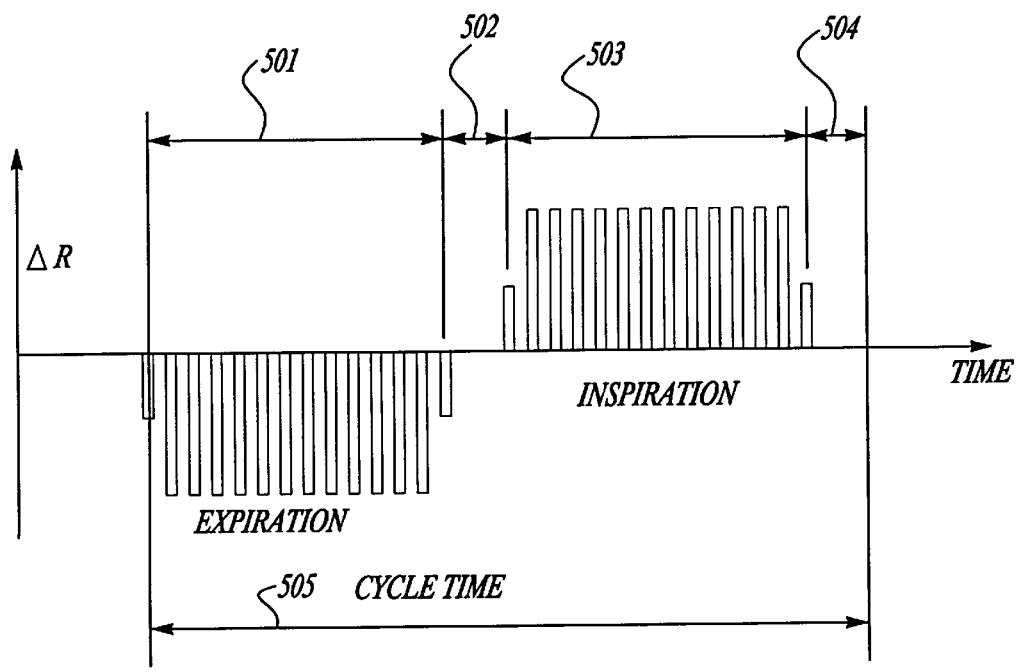
FIG. 4 is a timing diagram showing the output of sensor 144 of FIG. 1 in relation to a typical respiratory pattern.

Further details of appliance 120 and associated mouth cover 400 are set forth in FIGS. 3A, 3B and 4. Opening 130 of FIG. 1 preferably, as shown in FIG. 3B comprises a plurality of openings at an end of appliance 120 positioned furthest inward of the mammal's oral cavity.

Mouth cover 400 of FIGS. 3A, and 3B may take a variety of contoured shapes suitable for comfortable and leakless coupling of the partial vacuum to interior 132 of appliance 120 via conduit 121. Holes 410 and 420 in cover 400 are provided for receipt of a strap (not shown) which would encircle the patient's head to keep the mouth cover in place.

An additional embodiment of the invention is set forth in the functional block diagram of FIG. 5. The arrangement of FIG. 5 has many common features with the system of FIG. 1, but with the addition of a positive or pressurized supply of air for application to the oral/throat cavity during expiration periods.

In the system of FIG. 5, the human or mammalian body 500 has an appropriately coupled respiration sensor 544 and an oral appliance 520. A programmed controlling unit 550 is coupled for receipt of signals from the respiration sensor 544. Controlling unit 550 sets the flow position of a flow valve or switch 560 and can additionally set predetermined levels of vacuum and pressurized air via controlling unit outputs coupled to a first pressure regulator 580a and a second pressure regulator 580b.

Regulator 580a controls the vacuum level in chamber 570a which is evacuated by a vacuum air source 510. Pressure regulator 580b controls the pressure level in chamber 570b which is supplied from a pressurized air source 590.

Flow valve or switch 560, under the control of unit 550, applies either a predetermined vacuum level or a predetermined air pressure to the body's oral cavity via appliance 520.

In operation, this system, in addition to applying at least a partial vacuum during periods of inspiration, additionally applies positive pressure via the oral appliance during periods of expiration.

The invention has been described with reference to an exemplary embodiment solely for the sake of example. Those skilled in the art will recognize that variations can be made to this specific example. The scope and spirit of the invention is defined by the appended claims.

I claim:

1. A method for inducing pressure changes in a mouth and throat cavity of a mammal comprising the steps of:

monitoring a respiration pattern of the mammal to determine a first time period during which the mammal is inhaling and a second time period during which the mammal is exhaling;

inducing at least a partial vacuum in the mammal's mouth and throat during the first time period; and removing the at least partial vacuum during the second time period.

2. The method of claim 1 further comprising the step of inducing a positive pressure in the mammal's mouth during the second time period.

3. The method of claim 1 wherein the step of removing includes applying atmospheric pressure in the mammal's mouth.

4. Apparatus for inducing pressure changes in a mouth and throat cavity of a mammal, the apparatus comprising:

a vacuum source having a controlled output;

an appliance in fluid communication with the controlled output of the vacuum source, the appliance adapted for placement in a mouth of a mammal so as to be in fluid communication therewith;

a sensor adapted to be coupled to a preselected portion of the mammal's anatomy and operative to generate a first signal whenever the mammal inhales and a second signal whenever the mammal exhales;

a controller having an output coupled to the controlled output of the vacuum source, and at least one input coupled for receipt of the first and second signals, the controller operative, upon receipt of the first signal, to cause the controlled output to pull at least a partial vacuum in the appliance, and the controller operative, upon receipt of the second signal, to cause the controlled output to cease pulling the at least partial vacuum.

5. The apparatus of claim 4 wherein the appliance comprises a conduit having a first end coupled to the controlled output of the vacuum source and a second end adapted for insertion into the mouth of the mammal.

6. The apparatus of claim 5 wherein the appliance further comprises an appliance coupled to the second end of the conduit and shaped for receipt by the mouth of the mammal, the appliance including at least one opening enabling fluid communication between the conduit and at least a portion of the mouth.

7. The apparatus of claim 6 wherein the appliance includes a plurality of openings arranged in a predetermined pattern, the plurality of openings enabling the fluid communication between the conduit and at least a portion of the mouth.

8. The apparatus of claim 4 wherein the sensor comprises a variable electrical impedance element coupled to the mammal's anatomy in a manner such that the impedance element exhibits a first impedance value change whenever the mammal is inhaling and a second impedance value change whenever the mammal is exhaling.

9. The apparatus of claim 8 wherein the sensor further comprises a belt having first and second ends, the belt adapted for placement around an abdominal cavity of the mammal, and wherein the variable electrical impedance element comprises a variable resistor having a fixed terminal coupled to the first end of the belt and a movable terminal coupled to the second end of the belt.

10. The apparatus of claim 9 further comprising a return spring coupled between the fixed and movable terminals of the variable resistor.

11. Apparatus for inducing pressure changes in a mouth and throat cavity of a mammal, the apparatus comprising:

a regulated vacuum source having a controlled output;

a fluid switch having first, second and third ports, the first port coupled in fluid communication with the controlled output, and the second port coupled in fluid communication with ambient atmosphere;

an appliance in fluid communication with the third port of the fluid switch, the appliance adapted for placement in a mouth of a mammal so as to be in fluid communication therewith;

a sensor adapted to be coupled to a preselected portion of the mammal's anatomy and operative to generate a first signal whenever the mammal inhales and a second signal whenever the mammal exhales;

a controller having an output coupled to the fluid switch and having at least one input coupled for receipt of the first and second signals, the controller operative, upon receipt of the first signal, to cause the fluid switch to fluidly couple the first port to the third port, and the controller operative, upon receipt of the second signal, to cause the fluid switch to fluidly couple the second port to the third port.

12. Apparatus for inducing pressure changes in a mouth and throat cavity of a mammal, the apparatus comprising:

a regulated vacuum source having a controlled vacuum output;

a regulated pressurized air source having a controlled pressurized air output;

a fluid switch having first, second and third ports, the first port coupled in fluid communication with the controlled vacuum output and the second port coupled in fluid communication with the pressurized air output;

an appliance in fluid communication with the third port of the fluid switch, the appliance adapted for placement in a mouth of a mammal so as to be in fluid communication therewith;

a sensor adapted to be coupled to a preselected portion of the mammal's anatomy and operative to generate a first signal whenever the mammal inhales and a second signal whenever the mammal exhales;

a controller having an output coupled to the fluid switch and having at least one input coupled for receipt of the first and second signals, the controller operative, upon receipt of the first signal, to cause the fluid switch to fluidly couple the first port to the third port, and the controller operative, upon receipt of the second signal, to cause the fluid switch to fluidly couple the second port to the third port.

* * * * *

UNITED STATES PATENT AND TRADEMARK OFFICE
CERTIFICATE OF CORRECTION

PATENT NO. : 5,970,976
DATED : October 26, 1999
INVENTOR(S) : Hongwei Zhao It is certified that error appears in the above-identified patent and that said Letters Patent is hereby corrected as shown below:

Title Page, under "References Cited" insert --Other Publications -Human Central Propulsion, JAMA, Vol. 246, No. 18, Nov. 16, 1981, Shields, et al.--.

Signed and Sealed this

Nineteenth Day of September, 2000

Attest:

Q. TODD DICKINSON

*Attesting Officer*  *Director of Patents and Trademarks*